United States Patent
Chisholm et al.

[11] Patent Number: 5,157,147
[45] Date of Patent: Oct. 20, 1992

[54] METHOD FOR PREPARING MERCAPTOPROPIONIC ACID ESTERS

[75] Inventors: Daniel R. Chisholm, Warwick, N.Y.; George A. Seubert, Jr., Hamburg, N.J.

[73] Assignee: Witco Corporation, New York, N.Y.

[21] Appl. No.: 609,479

[22] Filed: Nov. 5, 1990

[51] Int. Cl.$^5$ .............................................. C07C 67/30
[52] U.S. Cl. ...................................... 560/147; 562/512
[58] Field of Search ................ 560/147, 145; 562/512

[56] References Cited

U.S. PATENT DOCUMENTS

| | | | |
|---|---|---|---|
| 4,052,440 | 10/1977 | Gladstone et al. | 560/154 |
| 4,067,901 | 1/1978 | Gladstone et al. | 560/147 |
| 4,307,225 | 12/1981 | Louthan | 528/279 |

Primary Examiner—Jose G. Dees
Assistant Examiner—Vera C. Clarke
Attorney, Agent, or Firm—Lockwood, Alex, FitzGibbon & Cummings

[57] ABSTRACT

A process is provided for the preparation of mercaptopropionic acid esters by reaction of an acrylic acid ester with hydrogen sulfide in the presence of a weakly basic amine as a catalyst, a polyether as a co-catalyst, a polythiodipropionic acid ester as a reactive solvent, and added elemental sulfur.

21 Claims, 1 Drawing Sheet

FIG. I
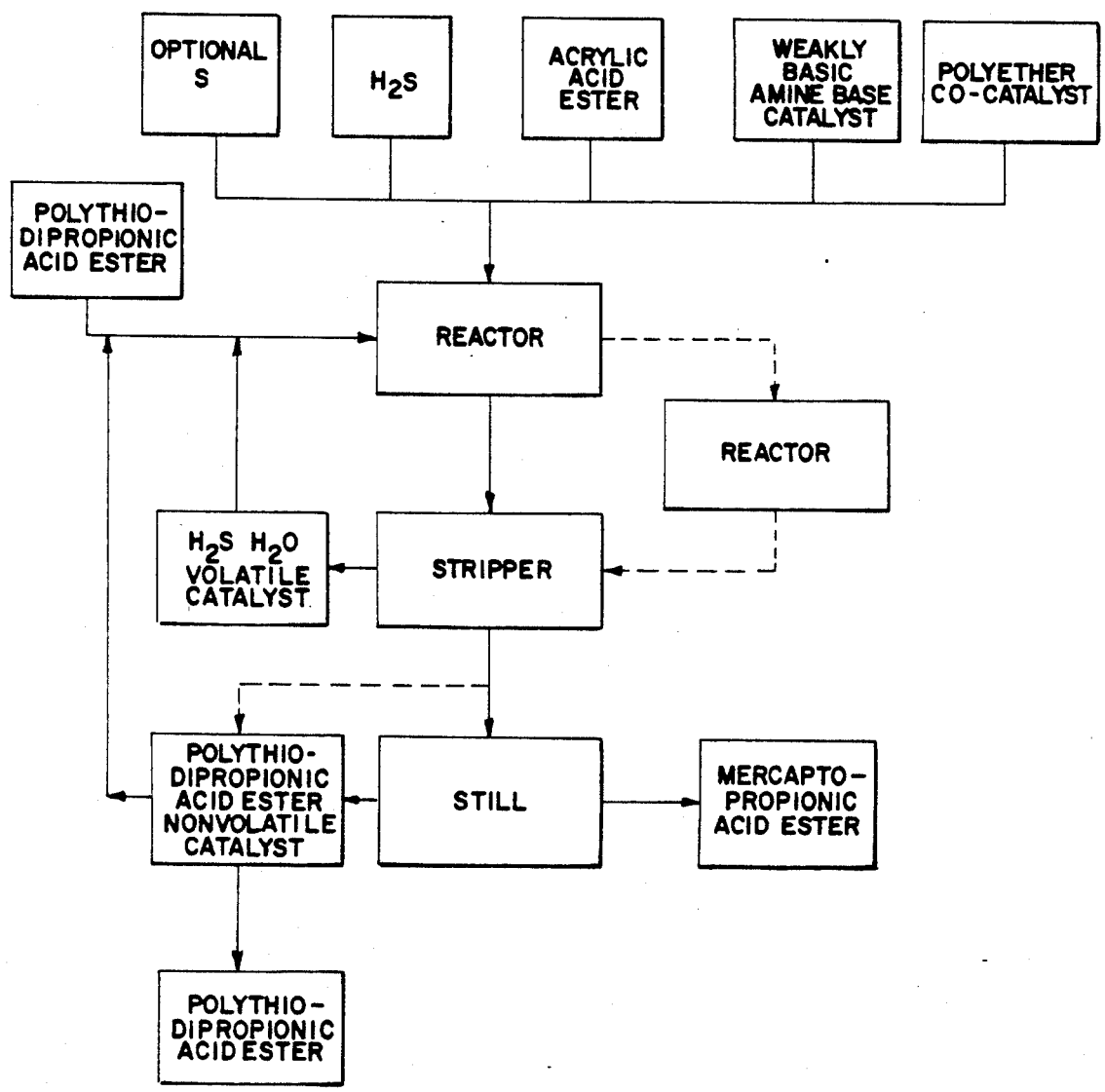

METHOD FOR PREPARING MERCAPTOPROPIONIC ACID ESTERS

BACKGROUND OF THE INVENTION

This invention generally relates to mercaptopropionic acid esters and, more particularly, to methods which are especially adapted for providing improved yields of mercaptopropionic acid esters.

U.S. Pat. No. 4,052,440 and 4,067,901 disclose methods for forming relatively high yields of mercaptopropionic acid esters and/or dithio dipropionic acid esters and higher polythio dipropionic acid esters by reaction of acrylic acid esters with hydrogen sulfide in the presence of a weakly basic amine catalyst and a polythio dipropionic acid ester in an amount of at least 30% by weight of the total monothiodipropionic acid ester and polythio dipropionic acid ester present. The polythio dipropionic acid ester is reactive, and takes part in the reaction, with a material improvement in the course of the reaction, and particularly in the yield of the mercaptopropionic acid ester, when the amount of polythio propionic acid ester is at least 30% by weight.

The overall reaction for preparing mercapto propionic acid ester can be set forth by the following equation.

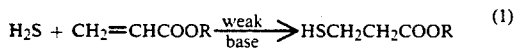

$$H_2S + CH_2=CHCOOR \xrightarrow[\text{base}]{\text{weak}} HSCH_2CH_2COOR \quad (1)$$

In this reaction (1) and in reactions (2), (3), (4) and (5), R is a hydrocarbon group, alkyl, aralkyl, cycloalkyl, or alkylcycloalkyl, having from one to eight carbon atoms.

Under the conditions of the processes disclosed in U.S. Pat. Nos. 4,052,440 and 4,067,901, the above reaction is favored, and the mercaptopropionic acid ester is obtained in good yield. However, the reaction system is extremely complex. A number of other reactions take place concurrently, some of which have been verified, and some of which are postulated from the reaction products that are obtained in the court of the reaction. Under controlled conditions other than those specified for the preparation of mercaptopropionic acid ester, the balance of the reactions can be so controlled that the predominant reaction products is not mercaptopropionic acid ester but dithiodipropionic acid ester, and higher polythiodipropionic acid esters, together with by-products, such as monothiodiproprionic acid esters.

In one important concurrent and consequential side reaction, the mercaptopropionic acid ester reacts with acrylic acid ester to form a monothiodipropionic acid ester, in accordance with the following reaction.

$$HSCH_2CH_2COOR + CH_2=CHCOOR \xrightarrow[\text{base}]{\text{weak}} \quad (2)$$

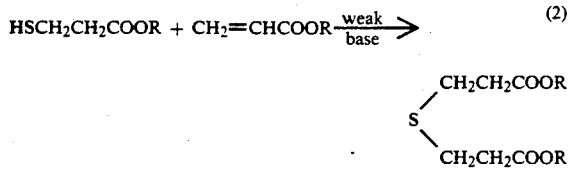

Although monothiodipropionic acid esters are useful materials, their concurrent production reduces the yield of the desired mercaptopropionic acid ester. Furthermore, if purity of the mercaptopropionic acid ester is important, the presence of an monothiodipropionic acid ester is a complicating factor because of the difficulty of making a clean separation between the two products.

It is apparent from reaction (2) that in the preparation of the mercaptopropionic acid ester, it is desirable to minimize the formation of monothiodipropionic acid esters. This can theoretically be accomplished in a number of ways. For example, the mercaptopropionic acid ester could be removed as soon as possible, preferably as rapidly as it is formed, from the reaction system, so as to avoid reaction of the product with the acrylic acid ester to form the monothiodipropionic acid ester. This approach can be effective within practical limitations. Another approach is to increase the reaction rate of reaction (1) and thereby reduce the availability of alkyl acrylate for, or otherwise disfavor, reaction (2) and other undesirable side reactions.

U.S. Pat. No. 4,307,225 discloses a reaction of olefinically unsaturated alkyl carboxylates such as methyl acrylate with hydrogen sulfide in the presence of a basic catalyst such as ammonium hydroxide, a lower alcohol such as methanol, and sulfur to yield a mixture of alkyl mercapto carboxylate, dialkyl thiodicarboxylate and dialkyl dithiodicarboxylate, which subsequently undergoes a transesterification reaction with a glycol such as polyether glycol to yield a polymer useful as a sealant.

It has been discovered that the use of a small percentage (approximately 2% by weight) of methanol in the processes of U.S. Pat. Nos. 4,052,440 and 4,067,901 enhances the rate of reaction of methyl acrylate with hydrogen sulfide (reaction (I)) and can suppress some undesirable side products. The lower alcohols such as methanol, however, are not readily acceptable for continuous processes because they tend to distill with the desired product requiring constant addition of methanol to the system or means for recycling the methanol. It has further been discovered that the use of a polyether co-catalyst in the process of U.S. Pat. Nos. 4,052,440 and 4,067,901 provides excellent results without the drawbacks of the lower alcohols.

It is accordingly, a general object of the present invention to provide a method of preparing mercaptopropionic acid esters.

Another object of the present invention is to improve upon the method of preparing mercaptopropionic acid esters disclosed in U.S. Pat. Nos. 4,052,440 and 4,067,901.

Another object of the present invention is to provide an improved continuous process for preparing mercaptopropionic acid esters.

These and other objects of the present invention will be apparent from the following detailed description.

DESCRIPTION OF THE DRAWINGS

FIG. 1 shows a flow diagram illustrating the formation of the principal reaction products of the process.

SUMMARY OF THE INVENTION

In accordance with this invention, high yields of mercaptopropionic acid esters are formed by reacting acrylates with hydrogen sulfide in the presence of a polythio dipropionic acid ester, a weakly basic amine catalyst and a polyether co-catalyst.

The polyether co-catalyst preferably has at least two ether oxygen atoms and more preferably has four or more oxyethylene groups. The polyether co-catalyst optionally contains alcoholic hydroxyl groups and preferably contains zero to two alcoholic hydroxyl groups. The polyether co-catalyst preferably, also, has a relatively high boiling point, of approximately 250° C. or greater.

DETAILED DESCRIPTION OF THE INVENTION

As set forth in U.S. Pat. No. 4,052,440 and 4,067,901, the disclosures of which are incorporated by reference, it is believed that the following correlated reaction sequence, results in the overall reaction indicated in reaction (1) above. First, the dithiodipropionic acid ester reacts with hydrogen sulfide, in accordance with the following equilibrium scheme:

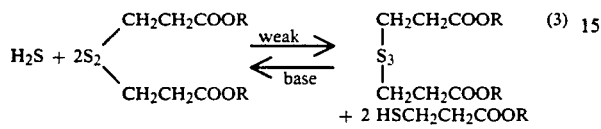
+ 2 HSCH$_2$CH$_2$COOR

It is for this reason that the dithiodipropionic acid ester solvent is referred to as a reactive solvent. It clearly takes part in the reaction, and can lead to an increase in yield.

This is followed by reaction of the hydrogen sulfide and acrylic acid ester with the trithiodipropionic acid ester thus formed.

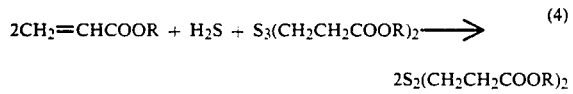

$$2S_2(CH_2CH_2COOR)_2$$

It appears that the acrylic acid ester reacts with hydrogen sulfide more readily in the presence of trithiodipropionic acid ester than with the mercapto compounds present in the reaction mixture. The presence of some sulfur, therefore, ensures that polythiodipropionic acid ester is present initially. Addition of small quantities of sulfur either continuously or from time to time helps to maintain a small concentration of trithiodiproprionic acid ester at all times.

Therefore, in this complex system, elemental sulfur has an important and in some respects essential effect if higher polythiodipropionic acid esters are desired. In amounts less than this, sulfur can enhance the yield of mercapto propionic acid ester and diminish the yield of the undesired monothiodipropionic acid ester, which can be important when, as here, mercaptopropionic acid ester is the desired product.

The formation of the higher polythiodipropionic acid esters proceeds by the following reactions.

The mercaptopropionic acid ester can react with sulfur in the presence of the weakly basic amine catalyst such as ammonia, to form dithiopropionic acid ester and higher polythiodipropionic acid ester, according to the amount of sulfur.

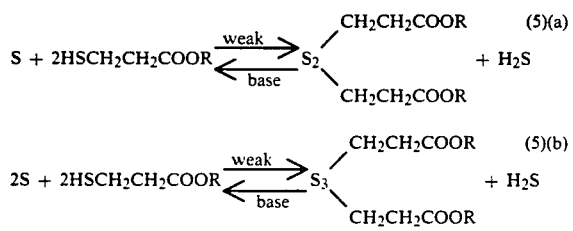

Sulfur also reacts with dithiodipropionic acid ester to form trithio and higher polythiodipropionic acid esters:

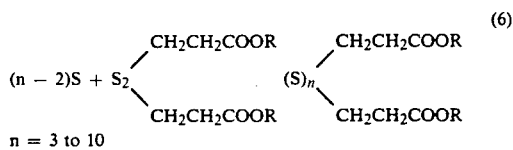

n = 3 to 10

In general, the preferred amount of sulfur is an amount within the range from about 0.01 to about 0.5 and preferably from about 0.03 to about 0.05 mole per mole of acrylic acid ester which decreases the proportion of monothio dipropionic acid ester, and enhances the ratio of dithio dipropionic acid ester plus mercaptopropionic acid ester to the monothio dipropionic acid ester. At amounts in excess of 0.05 mole, and especially in excess of 0.5 mole per mole of acrylic acid ester, the total proportion of dithiodipropionic acid ester and higher polythiodipropionic acid ester increases.

The process of the invention is illustrated in the flow sheet represented by FIG. 1 which shows the formation of the principal reaction products of the process, alternatively, sequentially or simultaneously: mercapto propionic acid ester and dithiodipropionic acid ester or higher polythiodipropionic acid ester, starting from hydrogen sulfide, acrylic acid ester, the weakly basic amine catalyst the polyether co-catalyst and sulfur.

The reactants are blended together in the proportions to give the desired product in a reactor, where they are held under conditions controlled to form the desired product. If desired, several reactors can be used in series or in parallel, and the addition of one such in-series reactor is shown by the alternative dashed lines in the flow sheet.

The completed reaction product is transferred to a stripper, where the unreacted hydrogen sulfide and any volatile catalyst(s), together with any water are removed. The residue is composed of mercaptopropionic acid ester, the solvent, dithio or polythio dipropionic acid ester, any nonvolatile catalyst and other by-products, as shown in the above equations.

If, as here, mercaptopropionic acid ester is to be isolated as the reaction product, the residue from the stripper is transferred to a still, where the mercaptopropionic acid ester is distilled off in vacuo. The residue, which also contains any nonvolatile catalyst, can then be recycled as a solvent for the reaction to the reactor.

If the desired product were the dithio or polythio dipropionic acid ester, then the residue from the stripper need not be transferred to a still, but instead could be worked up by removal of any nonvolatile catalyst as the desired product, since under the reaction conditions appropriate for formation of the dithio or polythio dipropionic acid ester, the mercaptopropionic acid ester would be present only in negligible amounts.

The operation of the process can be continuous or batchwise, as may be preferable according to available equipment.

Experimental evidence tends to show that the reaction of mercaptopropionic acid ester with acrylic acid ester (reaction (2) above) is favored by a higher temperature, more so than the reaction of acrylic acid ester and hydrogen sulfide. Accordingly, a low reaction temperature favors the formation of mercaptopropionic acid ester. Thus, low reaction temperatures are used to produce the desired mercaptopropionic acid ester product. In general, reaction temperatures within the range from about 0° to about 40° C. are preferred for mercaptopropionic acid ester formation. However, significant amounts of mercaptopropionic acid ester are formed at reaction temperatures up to 75° C.

At reaction temperatures in excess of 40° C., significant quantities of the monothiodipropionic acid ester begin to be formed, and at temperatures within the range from about 60° C. to about 150° C., reaction (2) consumes an increasing proportion of mercaptopropionic acid ester, formed in reaction (1). Thus, while reaction temperatures within the range from about 0° to about 150° C. can be used, the higher reaction temperatures within the range from about 75° to about 150° C. are not preferred for mercaptopropionic acid ester formation.

The formation of mercaptopropionic acid ester is also favored by a high hydrogen sulfide:acrylic ester molar ratio. If the hydrogen sulfide:acrylic ester molar ratio falls below 1:1, then reaction (1) is slowed in proportion to reaction (2), and relatively large amounts of the monothiodipropionic acid ester are obtained in reaction (2).

Accordingly, for the desired mercaptopropionic acid ester reaction product, the amount of hydrogen sulfide is in excess of the stoichiometric amount of 1:1 ratio and preferably in the ratio of 1.25:1 to 5:1 $H_2S$ to acrylic acid ester, required in reaction (1).

Since hydrogen sulfide is a gas, and is soluble in the reaction system only to a limited amount, ranging up to 3% by weight at atmospheric pressure and temperature, it may be desirable to carry out the reaction under a superatmospheric pressure of hydrogen sulfide, especially if mercaptopropionic acid ester is the desired product, since this has the effect of increasing the proportion of hydrogen sulfide in the reaction system. Accordingly, relatively high hydrogen sulfide pressure can be used, ranging up to about 500 psig. The reaction will proceed at atmospheric pressure, however, and normally the pressure will be within the range from atmospheric pressure to about 200 psig. The $H_2S$ concentration is within the range from about 0.1% to saturation in the reaction solvent under the reaction conditions.

The residence time is no way critical. The reaction proceeds rather rapidly at elevated temperatures, more slowly at lower temperatures. The reactants are of course kept in contact until an acceptable yield of the desired product is obtained. The residence time is normally within the range from about 10 minutes to about 5 hours, and preferably within the range from about ½ hour to about 2 hours, under the reaction conditions set forth above.

The reaction with $H_2S$ proceeds with any acrylic acid ester having from one to about eight carbons in the ester substituent, such as methyl acrylate, ethyl acrylate, propyl acrylate, isopropyl acrylate, butyl acrylate, isobutyl acrylate, sec-butyl acrylate, tert-butyl acrylate, amyl acrylate, isoamyl acrylate, hexyl acrylate, heptyl acrylate, octyl acrylate, isooctyl acrylate and 2-ethyl hexyl acrylate, as well as the corresponding alkyl methacrylate and crotonate esters.

The reaction proceeds in the presence of a weakly basic catalyst, preferably a weakly basic amine catalyst, and a polyether co-catalyst.

The weakly basic amine catalyst, includes ammonia and organic amines, both the open chain or aliphatic and cyclic amines, and the cyclic amines include the heterocyclic amines with the nitrogen atom in the ring, and the carbocyclic amines with the amine nitrogen attached to the ring.

By "weakly basic" it is meant that the compound is more alkaline than aniline and less alkaline than alkali metal hydroxide. The "weakly basic" amine catalysts that are effective in the process of the invention react reversibly with $H_2S$ in the way that ammonia and $H_2S$ make ammonium sulfide which readily regenerates $H_2S$ and ammonia on heating. Less basic materials (e.g. aniline) do not react with $H_2S$ and strong bases react with $H_2S$ irreversibly. Quaternary bases are often thought of as strong bases but are decomposed by heating so that their reaction with H2S is also reversible. Other weakly basic catalysts include compounds such as sodium hydrosulfide, NaSH.2H20 which is less alkaline than sodium hydroxide.

Ammonia can be used as ammonia gas or, conveniently, in aqueous solution as ammonium hydroxide or ammonium sulfide. The concentration of ammonia in the catalyst is not critical, and is normally within the range from about 20 to about 100%. Any desired concentration can be used, since the important factor is not the ammonia concentration in ammonium hydroxide, but the proportion of ammonia in the reaction system which is suitably from about 0.1% to about 10% by weights as $NH_3$.

The organic amines that can be used are defined by the formula

(a)

Quaternary amines can also be used, as defined by the formula

(b)

In the above formulae, $R_1$, $R_2$ and $R_3$ represent hydrogen or hydrocarbon groups having from one to about eighteen carbon atoms in the organic amine of formula (a) and at least one R is not hydrogen, and $R_4$, $R_5$, $R_6$ and $R_7$ are hydrocarbon group having from one to eighteen carbon atoms. The R groups may be taken singly, as alkyl, cycloalkyl, cycloalkyl alkyl, and alkaryl groups, or two or more R groups may be taken together with the nitrogen to form a heterocyclic ring with the nitrogen atom in the ring.

While the R groups individually may have up to 18 carbon atoms, the R groups in the amine or quaternary amine should not in the aggregate total more than 30 carbons.

X represents hydrosulfide HS-, or sulfide S, or any basic anion of the inorganic or organic type, such as OH—, $HCO_3$—, and $CO_3$=.

The R substituents may also include one or more hydroxy groups-OH and/or one or more ether groups-O-, and/or one or more ester groups -COOR.

Exemplary R alkyl groups include methyl, ethyl, propyl, isopropyl, butyl, isobutyl, tertiary, butyl, amyl, isoamyl, hexyl, isohexyl, heptyl, isoheptyl, octyl, tertiary-octyl, 2-ethylhexyl, isooctyl, nonyl, decyl, dodecyl, hexadecyl, tridecyl, tetradecyl and octadecyl. R alkenyl groups include propenyl, butenyl, pentenyl, hexenyl, hepotenyl, octenyl, nonenyl, decenyl, dodecenyl, ricinoleyl, linoleyl. and linolenyl.

Hydroxyl-containing alkyl groups include hydroxyethyl, hydroxypropyl, hydroxyamyl and hydroxyhexyl. As the alkyl substituent to which the hydroxyl is attached becomes longer than six carbon atoms, the effect of the hydroxyl group lessens, and becomes almost negligible.

Ether-containing alkyl groups include ethoxyethyl, ethoxypropyl, propoxypropyl, butoxyethyl, amyloxyamyl, decyloxyethyl, dodecyloxyethyl, octyloxyoctyl.

Ester-containing groups include carboethoxy methyl, carbomethoxy ethyl, and carboethoxy ethyl.

Cycloalkyl R groups include cyclopropyl, cyclobutyl, cyclopentyl, cyclohexyl, cycloheptyl and cyclooctyl.

Heterocyclic groups in which two R's are taken together to form a heterocyclic ring which contains the nitrogen in the molecule include piperdine, pyridine, pyrrolidine, pyrazolidine, piperazine, triethylenediamine, pyrrolizine, morpholine, N-methyl morpholine, N,N-dimethyl piperazine and N-ethyl morpholine.

Exemplary amines include methyl amine, ethyl amine, propyl amine, isopropyl amine, butyl amine, amyl amine, hexyl amine, heptyl amine, octyl amine, decyl amine, dodecyl amine, myristyl amine, palmityl amine, stearyl amine, monoethaneolamine, dimethyl amine, methyl ethyl amine, diisoproyl amine, dibutyl amine, dihexyl amine, dioctyl amine, butyl hexyl amine, didecyl amine, didodecyl amine, propylamyl amine, diethanolamine, dipropanolamine, dihexanolamine, trimethyl amine, triisopropyl amine, tributyl amine, methyl diethyl amine, dimethyl ethyl amine, methyl ethyl propyl amine, triamyl amine, triisobutyl amine, trihexyl amine, trioctyl amine, tridecyl amine, methyl hexyl decyl amine, dodecyl dimethyl amine, octadecyl dimethyl amine, triethanolamine, triisopropanolamine, tributanolamine, diethyl cyclohexylamine, dimethyl ethanol amine, cyclohexyl amine, dicyclohexyl amine, methyl cyclohexyl amine, ethyl cyclopentyl amine, tricyclohexyl amine, dicyclopentyl hexyl amine, cyclopropyl methyl amine, cycloheptyl amine, cyclopentyl amine, tetramethyl- 1,4-butane diamine, ethylene diamine, diethylene triamine, tetramethyl ethylene diamine, N-tetradecyl propylene diamine, N-stearyl propylene diamine, glycine ethyl ester, methyl 3-dimethylaminopropionate, tetramethyl ammonium carbonate, stearylpyridinium hydroxide, cetyl dimethyl benzyl ammonium hydroxide, dimethyl morpholinium sulfide, oleyl triethyl ammonium hydroxide, methyl ethyl isopropyl isobutyl ammonium hydrosulfide and choline bicarbonate.

The concentration of weakly basic amine catalyst can be rather small. As little as 0.1% (by weight of the reaction mixture) is effective. The amount can extend up to 10%, although such large amounts are not normally required. A preferred amount is within the range from about 0.2% to about 3%. In the case of ammonia, from 1 to 2% is preferred.

The polyether co-catalyst is generally defined as a polyether having at least two ether oxygen atoms and optional alcoholic hydroxyl groups. Preferably, the polyether has four or more oxyethylene groups. The polyether preferably contains zero to two alcoholic hydroxyl groups. The polyether also preferably has a relatively high boiling point, of approximately 250° C. or greater, to minimize its codistillation with the desired product.

The polyether co-catalyst can be generally represented by the formula:

$$XO(CHRCH_2O)_nY \qquad (I)$$

wherein R assigned individually each time is hydrogen or methyl, n is at least 3 and can be as high as available materials practically allow, X and Y are hydrogen or organic groups preferably with the possibility of being joined together in a ring. X, R and Y can all be hydrogen. Some representative polyether co-catalysts according to Formula I are listed in Table I below:

TABLE I

| NAME | n | R | X | Y |
|---|---|---|---|---|
| Tetraethylene glycol | 4 | H | H | H |
| Tripropylene glycol | 3 | $CH_3$ | H | H |
| 8000 MW polyethylene glycol | 181 | H | H | H |
| 4000 MW polypropylene glycol | 69 | $CH_3$ | H | H |
| Nonylphenol ethoxylate (30EO) | 30 | H | H | $-C_6H_4C_9H_{19}$ |
| Secondary alcohol ethoxylate | 15 | H | H | sec-$C_{12}H_{25}$ |
| Tertiary mercaptan ethoxylate | 10 | H | H | $CH_2CH_2S-C_{12}H_{25}(tert)$ |
| Ethylene oxide-propylene oxide block copolymer · 11000MW | 48 | $CH_3$ | H | $(OCH_2CH_2)90(CH_2CH_2)900H$ |
| 1,4,7,10,13,16-hexaoxacyclooctadecane | 5 | H | $-CH_2CH_2-$ | (X + Y) |

It is hypothesized, without being limited to any particular theory of the invention, that the function of the co-catalyst is to complex with the cation (e.g. ammonium) and thereby make the anion more reactive. Introduction of branching in the polyether as in poly(propylene glycol) or changing the separation of the oxygen atoms in the polyether as in poly(tetrahydrofuran) appears to decrease the efficiency of the co-catalyst and, accordingly, is not preferred. Preferred polyether co-catalysts contain at least four consecutive oxyethylene units such as found in poly(ethene glycol). Crown ethers, such as 18-CROWN-6 (1,4,7,10,13,16-hexaoxacyclooctadecane) have been found to be especially preferred.

The polyether co-catalyst is present in effective amounts. Depending on the amount of weakly basic amine catalyst present as little as 0.1% (by weight of the reaction mixture) of the polyether co-catalyst may be effective and amounts of the polyether co-catalyst can extend up to 10%, although such large amounts are not normally required. A preferred amount is within the range from about 0.2% to about 3%. The polyether co-catalyst can be provided to the reaction in a variety of ways. For example, in continuous processes the polyether co-catalyst can be added to the reaction solvent.

It has been previously considered that an aqueous phase is essential to proper catalyst solubility. However, such use of aqueous systems has made the production of mercaptans from acrylic acid esters and hydrogen sulfide impossible. In the process mercaptans in substantial yields are obtained using as the solvent a dithiodipropionic acid ester or polythiodipropionic acid ester or mixture thereof. Since no aqueous phase is required, hydrolysis of the raw material and of the product, thus reducing yields, does not take place. In the instant process, the reaction medium is a single phase of dithio and/or polythio dipropionic acid ester, in which the acrylic ester, hydrogen sulfide and sulfur are dissolved. For the desired mercaptopropionic acid esters, the reaction medium solvent should be dithiodipropionic acid ester; if trisulfide dipropionic acid ester is desired, the reaction medium should be trisulfide dipropionic acid ester, etc. A small amount of water (to keep catalyst in solution) may be used, insufficient to lead to hydrolysis. The amount of water is less than 5% and preferably less than 2 5%; the system is essentially nonaqueous. If a gas phase catalyst is used, no water need be present to dissolve the catalyst.

Since the system is essentially nonaqueous, there is no disposal problem, such as occurs with aqueous systems containing ammonium mono or polysulfides or sodium sulfide derivatives. The reaction mixture can be worked up in a single distillation that yields both primary components in 90% or purer form, the mercaptan as distillate, and the dithio and/or polythio dipropionic acid ester as still bottoms.

The following process details are for a high-yield system for preparing either mercaptopropionic acid ester or dithiodipropionic acid ester.

A reaction medium of dithiodipropionic acid ester is provided.

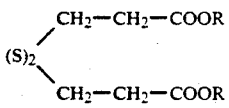

Hydrogen sulfide gas is bubbled into and dissolved therein to within the range from about an at least 0.1% by weight concentration up to the saturation point (about 2-3% by weight, at atmospheric conditions). Slight heat may be added but the reaction will proceed at any temperature within the range from 0° to 150° C. In any case, the temperature should be below about 75° C., and above about 0° C. The pressure on the system is determined mainly by the concentration of dissolved $H_2S$ desired, and is not critical. Pressures of hydrogen sulfide of from 200 to 500 psig. can be used. Atmospheric pressure can be used at the lower $H_2S$ concentrations.

To this reaction medium one or more acrylic acid esters $CH_2=CH-COOR$ are added at about 1 lb./hr./gal. reaction medium. The rate of addition should not exceed 10 lb./hr./gal. since local excesses of acrylic ester are to be avoided. R is hydrocarbon, e.g. alkyl, having from one to eight carbon atoms. It is possible to use mixed esters if asymmetric dithio and/or polythio dipropionic acid esters are desired, or if mixed mercaptopropionic acid esters are desired.

A weakly basic amine is added in an amount to give alkaline conditions for the reaction. Preferably, $NH_3$ is used, but also primary, secondary, tertiary or quaternary amines can be used. In addition, $NH_3$ can be in the form of an aqueous ammonium hydroxide solution, added separately or added the medium containing $H_2S$. From 0.1 to 10% by weight of base is used, preferably 1% in the case of $NH_3$.

A polyether co-catalyst is added in an effective amount. Preferably, poly(ethene glycol) or a crown ether such as 18-crown-6 (1, 4, 7, 10, 13, 16-hexaoxacyclooctadecane) is used. From 0.1 to 10% by weight of polyether co-catalyst is used, preferably 2% when $NH_3$ is used as the basic amine.

As the reaction begins the mercaptopropionic acid ester $HSCH_2CH_2COOR$ is formed. For this end product, the temperature should be maintained at from 0° to 40° C., and the acrylic acid ester should be added slowly (under 1 lb./hr./gal.), with stirring. If the $H_2S$ concentration in the reaction medium is increased by increasing the $H_2S$ pressure to from about 75 to 125 psig in a closed system, faster addition rates can be employed, e.g. up to 10 lb./hr./gal. The mercaptopropionic acid ester produced can be easily removed as product from the reaction medium by distillation as it is formed, or shortly thereafter.

The following Examples are offered to illustrate the present invention.

In general, in the following examples, methyl mercaptopropionate was prepared according to the following general reaction conditions: methyl acrylate (MA) containing 2% by weight co-catalyst was added to a stirred solution of dimethyl dithiodipropionate (DDD) containing 2% by weight co-catalyst at 50 psig $H_2S$. Anhydrous ammonia (0.3%) was used as the basic amine catalyst. The reactions were run at the below-noted temperatures. Samples were withdrawn from the reaction vessel after sufficient methyl acrylate had been added to make 10%, 20%, 30%, 40% and 50% respective amounts of methyl mercaptopropionate (MMP) based on the amount of solvent present. The samples were analyzed by GLC to determine the amounts of dimethyl 2,3' thiodipropionate (UDMD) and dimethyl 3,3'-thiodipropionate (DMD) byproducts present. The percentages set forth below for UDMD and DMD are the respective weight of byproduct formed divided by the theoretical weight of methyl mercaptopropionate that could be formed from the total weight of methyl acrylate added. It is believed that UDMD is formed as an uncatalyzed reaction byproduct of methyl acrylate and its relative percentage serves as an indicator of rate acceleration, i.e. a decrease in the percentage of UDMD indicates an increase in the rate of the base catalyzed reaction.

EXAMPLE 1

Preparation of methyl mercaptopropionate (MMP) was conducted according to the general reaction outlined above with methanol (2% by weight) added to the DDD and to the MA. The reaction was conducted between 30°–35° C. The amount of UDMD and DMD was monitored and compared to amounts of UDMD and DMD previously present when MMP was similarly prepared without methanol present.

| YIELD OF BYPRODUCT IN MMP PREPARATION (30-35° C.) | | | | |
|---|---|---|---|---|
| Theoretical | 2% Methanol | | No Methanol | |
| % MMP | % UDMD | % DMD | % UDMD | % DMD |
| 10 | 0 | 4.6 | 0.2 | 3.9 |
| 20 | 0 | 4.6 | 0.4 | 4.7 |
| 30 | 0 | 9.4 | 0.4 | 6.2 |
| 40 | .1 | 17.5 | 0.5 | 8.3 |
| 50 | .2 | 21.4 | 0.7 | 11.3 |

These data indicate that at similar temperatures and with similar reactants the addition of methanol reduces the amount of UDMD unwanted byproduct.

EXAMPLE 2

Methyl mercaptopropionate was prepared as in Example 1 but the reaction was conducted between 60°-65° C. The amount of UDMD and DMD was monitored and compared to amounts of UDMD and DMD previously present when MMP was similarly prepared without methanol present.

| YIELD OF BYPRODUCT IN MMP PREPARATION (60-65° C.) | | | | |
|---|---|---|---|---|
| | % UDMD | | % DMD | |
| Theoretical % MMP | 2% $CH_3OH$ | w/o $CH_3OH$ | 2% $CH_3OH$ | w/o $CH_3OH$ |
| 10 | 0.7 | 7.9 | 9.5 | 22.3 |
| 20 | 1.2 | 8.5 | 16.1 | 21.5 |
| 30 | 1.4 | 8.3 | 22.4 | 24.8 |
| 40 | 1.6 | 9.3 | 28.0 | 27.9 |
| 50 | 1.7 | 9.4 | 38.1 | 34.9 |

As in Example 1, these data indicate that at similar temperatures and with similar reactants the addition of methanol reduces the amount of UDMD byproduct.

EXAMPLE 3

Methyl mercaptopropionate was prepared according to the general reaction conditions with 2% by weight of each of the following components added to the DDD in separate reaction runs: water; methanol; glycerin; dipropylene glycol (DPG); tripropylene glycol (TRPG); tetraethylene glycol (TEG); and polyethylene glycol (PEG) (MW=300). The reactions were run at 60° C. and the amounts of UDMD and DMD were monitored and reported as follows:

| % UDMD BYPRODUCT FORMED AT 60° C./50 PSIG | | | |
|---|---|---|---|
| % MMP | $H_2O$ | METHANOL | GLYCERIN |
| 10 | 2.2, 1.7 | 1.7 | 2.5 |
| 20 | 2.6, 1.9 | 1.3 | 3.1 |
| 30 | 2.9, 2.4 | 1.7 | 3.6 |
| 40 | 3.6, 3.1 | 1.8 | 4.4 |
| 50 | 3.6, 3.1 | 2.2 | 4.5 |
| % MMP | DPG | TRPG | TEG | PEG |
| 10 | 0.4 | 0.9 | 0.2, 0.4 | 0.7 |
| 20 | 1.4 | 1.7 | 0.5, 0.6 | 0.5 |
| 30 | 1.6 | 1.8 | 0.6, 0.5 | 0.4 |
| 40 | 1.6 | 2.0 | 0.9, 0.9 | 0.5 |
| 50 | 1.9 | 2.2 | 1.0, 1.1 | 0.6 |

| % DMD BYPRODUCT FORMED AT 60° C./50 PSIG | | | |
|---|---|---|---|
| % MMP | $H_2O$ | METHANOL | GLYCERIN |
| 20 | 12.3, 12.3 | 13.1 | 12.1 |
| 30 | 18.0, 16.7 | 14.9 | 15.4 |
| 40 | 22.2, 24.2 | 20.1 | 20.2 |
| 50 | 27.9, 29.8 | 27.3 | 29.6 |
| % MMP | DPG | TRPG | TEG | PEG |
| 20 | 12.6 | 12.3 | 8.6, 9.5 | 9.4 |
| 30 | 17.0 | 16.7 | 11.1, 11.8 | 9.5 |
| 40 | 22.0 | 23.5 | 17.6, 16.6 | 12.4 |
| 50 | 29.6 | 31.0 | 19.5, 21.6 | 18.4 |

These data indicate that at similar temperatures and with similar reactants the use of DPG and TRPG reduces the amount of UDMD byproduct as well as methanol does, and that the use of TEG and PEG reduces the amount of UDMD byproduct better than methanol does.

EXAMPLE 4

The effect of temperature on byproduct formation during the production of methyl mercaptopropionate was studied by preparing MMP according to the general reaction conditions with and without polyethylene glycol (PEG) (MW=300) as a co-catalyst at several temperatures. The formation of UDMD and DMD was monitored and the results were as follows:

| NOMINAL | 30° NO PEG | | 30° PEG | | 45° PEG | | 60° NO PEG | | 60° PEG | |
|---|---|---|---|---|---|---|---|---|---|---|
| % MMP | UDMD | DMD | UDMD | DMD | UDMD | DMD | UDMD | DMD | UDMD | DMD |
| 10 | 0.1 | 5.8 | 0.2 | 3.2 | 0 | 1.4 | 1.7 | 13.6 | 0.7 | 11.7 |
| 20 | 0.2 | 6.3 | 0.1 | 3.3 | 0 | 2.6 | 1.9 | 12.3 | 0.5 | 9.4 |
| 30 | 0.3 | 7.4 | 0.1 | 4.1 | 0 | 5.0 | 2.4 | 16.7 | 0.4 | 9.5 |
| 40 | 0.3 | 8.1 | 0.1 | 5.6 | 0.1 | 7.6 | 3.1 | 24.2 | 0.5 | 12.5 |
| 50 | 0.3 | 10.1 | 0.1 | 7.1 | 0.1 | 9.8 | 3.1 | 29.8 | 0.6 | 18.4 |

These date indicate that at similar temperatures and with similar reactants the use of a polyether co-catalyst such as PEG reduces the amount of UDMD byproduct produced consistently across the temperatures studied. Thus, for example, with similar reactants, in the presence of PEG the reaction temperature can be raised from 30° to 45° C. without increasing the amount of byproduct formed without PEG at 30°.

EXAMPLE 5

Methyl mercaptopropionate was prepared according to the general reaction conditions with 2% by weight of the following components added to the DDD in separate reaction runs: poly(ethylene glycol) (PEG MW 8000); and poly(propylene glycol) (PPG MW 4000). The reactions were run at 65° C. to enhance the production of undesirable byproducts and the amounts of UDMD and DMD were monitored and compared to the amounts of UDMD and DMD monitored in Example 3 when tetraethylene glycol (TEG) was used as a co-catalyst and to previous results when no co-catalyst was used under similar reaction conditions. The results are reported as follows:

| BYPRODUCT FORMATION IN THE MMP REACTION 50 PSIG, 65° C. | | | | | | | |
|---|---|---|---|---|---|---|---|
| NOMINAL | PEG | | | | TEG | | NO CO-CATALYST | |
| % MMP | % UDMD | % DMD | % UDMD | % DMD | % UDMD | % DMD | % UDMD | % DMD |
| 20 | 1.0 | 5.2 | 4.2 | 14.6 | 0.6 | 9.5 | 7.3 | 19.9 |
| 30 | 1.4 | 9.0 | 4.5 | 17.1 | 0.5 | 11.8 | 7.1 | 21.3 |

-continued

| NOMINAL | PEG | | | | TEG | | NO CO-CATALYST | |
|---|---|---|---|---|---|---|---|---|
| % MMP | % UDMD | % DMD | % UDMD | % DMD | % UDMD | % DMD | % UDMD | % DMD |
| 40 | 1.5 | 13.2 | 4.8 | 21.2 | 0.9 | 16.6 | 8.0 | 23.6 |
| 50 | 1.8 | 20.6 | 5.1 | 26.8 | 1.1 | 21.6 | 8.0 | 30.0 |

BYPRODUCT FORMATION IN THE MMP REACTION 50 PSIG, 65° C.

These date indicate that at similar temperatures and with similar reactants the use of TEG and PEG reduces the amount of UDMD byproduct produced. The use of PPG as a co-catalyst provides improved results compared to the system without a co-catalyst but does not provide as good as results as those produced when TEG and PEG are used.

EXAMPLE 6

Methyl mercaptopropionate was prepared according to the general reaction with 2% by weight of each of the following components added to the DDD in separate reaction runs: poly(tetrahydrofuran)(PTHF); poly(vinyl alcohol)(PVA); and poly(ethylene glycol)-(PEG) (MW=8000). The reactions were conducted at 65° C. and the amounts of UDMD and DMD produced were monitored and reported as follows:

| NOMINAL | PTHF | | PVA | | PEG | |
|---|---|---|---|---|---|---|
| % MMP | % UDMD | % DMD | % UDMD | % DMD | % UDMD | % DMD |
| 20 | 3.2 | 14.2 | 2.6 | 12.4 | 1.0 | 5.2 |
| 30 | 3.6 | 17.3 | 3.3 | 16.2 | 1.4 | 9.0 |
| 40 | 4.1 | 20.9 | 3.6 | 20.0 | 1.5 | 13.2 |
| 50 | 4.1 | 26.3 | 5.1 | 25.3 | 1.8 | 20.6 |

These data indicate that at similar temperatures and with similar reactants PEG is better than is PTHF and PVA at reducing the amount of UDMD byproduct produced.

EXAMPLE 7

Methyl mercaptopropionate was prepared under the general reaction conditions at 65° C. except the DDD solvent was replaced with a 1:1 mixture of tetraethylene glycol and poly(ethylene glycol)(MW 300). It was determined that over 70% of the methyl acrylate was converted to DMD.

EXAMPLE 8

Methyl mercaptopropionate was prepared according to the general reaction conditions with 2% by weight of 18-CROWN-6 (1,4,7,10,13,16-hexaoxacyclooctadecane) added to the DDD as a co-catalyst. The reaction was conducted at 65° C. The amounts of UDMD and DMD produced were monitored and are compared below to amounts previously produced when PEG was used as a co-catalyst and when no co-catalyst was present.

| NOMINAL | 18 CROWN - 6 | | PEG | | NO CO-CATALYST | |
|---|---|---|---|---|---|---|
| % MMP | % UDMD | % DMD | % UDMD | % DMD | % UDMD | % DMD |
| 20 | 0 | 3.7 | 1.0 | 5.2 | 7.3 | 19.9 |
| 30 | 0 | 4.8 | 1.4 | 9.0 | 7.1 | 21.3 |
| 40 | 0 | 6.2 | 4.8 | 21.2 | 8.0 | 23.6 |
| 50 | 0 | 8.3 | 5.1 | 26.8 | 8.0 | 30.0 |

These data indicate that the addition of the crown ether effectively reduces the amount of UDMD byproduct produced in the system.

What is claimed is:

1. An improved process for preparing mercaptopropionic acid esters of the formula:

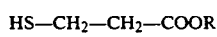

where R is selected from the group consisting of alkyl, cycloalkyl, and alkyl cycloalkyl having from one to eight carbon atoms, which comprises reacting hydrogen sulfide and an alcrylic acid ester o the formula:

in an essentially nonaqueous system containing less than 5% water and in the presence of a reactive solvent comprising polythiodipropionic acid ester of the formula

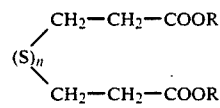

wherein n is a number from 2 to 10, the polythio-dipropionic acid ester being present in an amount of at least 30% by weight of the total of any monothiodipropionic acid ester and of the polythiodipropionic acid ester present; a weakly basic amine catalyst selected from the group consisting of ammonia, primary, secondary and tertiary amines and quaternary amines; the weakly basic amine catalyst being present in an amount within the range from about 0.1 to about 10% by weight of the reaction mixture; the reaction being carried out at a temperature within the range of from about 0° to about 150° C. and H2S concentration within the range from about 0.1% to saturation in the reactive solvent under the reaction conditions; wherein the improvement comprises conducting said reaction ion the presence of a polyether co-catalyst, the co-catalyst being present in the amount within the range from about 0.1 to about 10% by weight of the reaction mixture.

2. The process of claim 1 wherein the polyether is represented by the formula:

XO(CHR'CH$_2$O)$_m$Y wherein R' assigned individually each time is hydrogen or methyl, m is at least 3, X and Y individually are hydrogen or organic groups.

3. The process of claim 1 wherein the polyether contains at least four consecutive oxyethylene units.

4. The process of claim 1 wherein the polyether contains between 0 and 2 alcoholic hydroxyl groups.

5. The process of claim 1 wherein the polyether has a boiling point of approximately at least 250° C.

6. The process of claim 1 wherein the polyether is polyethylene glycol.

7. The process of claim 6 wherein the polyether is tetra ethylene glycol.

8. The process of claim 1 wherein the polyether is a crown ether.

9. The process of claim 8 wherein the polyether is 1,4,7,10,13,16-hexaoxacyclooctadecane.

10. The process of claim 1 wherein the polyether is a ring compound.

11. A process for preparing mercaptopropionic acid esters comprising reacting hydrogen sulfide and an acrylic acid ester of the formula:

CH$_2$=CH—COOR where R is selected from the group consisting of alkyl, cycloalkyl, and alkyl cycloalkyl having from one to eight carbon atoms, in an essentially nonaqueous system containing less than 5% water and in the presence of (a) a reactive solvent comprising polythiodipropionic acid ester of the formula

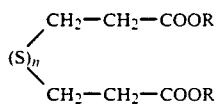

wherein n is a number from 2 to 10, the polythio-dipropionic acid ester being present in an amount of at least 30% by weight of the total of any monothiodipropionic acid ester and of the polythiodipropionic acid ester present; (b) a weakly basic catalyst, the weakly basic catalyst being present in an amount within the range from about 0.1 to about 10% by weight of the reaction mixture; and (c) a polyether catalyst represented by the formula:

XO(CHR'CH$_2$O)$_m$Y wherein R' assigned individually each time is hydrogen or methyl, m is at least 3, X and Y individually are hydrogen or organic groups, the co-catalyst being present in the amount within the range from about 0.1 to about 10% by weight of the reaction mixture; the reaction being carried out at a temperature within the range of from about 0° to about 150° C. and H$_2$S concentration within the range from about 0.1% to saturation in the reactive solvent under the reaction conditions.

12. The process of claim 11 wherein the polyether contains at least four consecutive oxyethylene units.

13. The process of claim 11 wherein the polyether contains between 0 and 2 alcoholic hydroxyl groups.

14. The process of claim 11 wherein the polyether has a boiling point of approximately at least 250° C.

15. The process of claim 11 wherein the polyether is polyethylene glycol.

16. The process of claim 11 wherein the polyether is tetra ethylene glycol.

17. The process of claim 11 wherein the polyether is a crown ether.

18. The process of claim 17 wherein the polyether is 1,4,7,10,13,16-hexaoxacyclooctadecane.

19. The process of claim 11 wherein the polyether is a ring compound.

20. The process of claim 11 wherein said system further includes elemental sulfur in an amount within the range of from about 0.01 to about 5 moles per mole of acrylic acid ester.

21. The process of claim 20 wherein the reaction is carried out at a temperature within the range of from about 0° to about 75° C., the elemental sulfur is present in an amount from about 0.01 to about 0.5 moles per mole of acrylic acid ester, and the hydrogen sulfide is present in an amount from about 1.25 to 5.0 moles per mole of acrylic acid ester.

* * * * *